United States Patent [19]

Weis-Fogh et al.

[11] Patent Number: 5,480,378
[45] Date of Patent: Jan. 2, 1996

[54] APPARATUS FOR PREPARING A CONCENTRATE OF COAGULATION FACTORS FROM A BLOOD SAMPLE

[76] Inventors: Ulla Weis-Fogh, 20 Mellemvang, DK-2970 Hørsholm; Niels E. Holm, 10B Julemosevej, DK-3460 Birkerød; Søren Hern, 41 Sommervej, DK-3520 Farum, all of Denmark

[21] Appl. No.: 295,145

[22] Filed: Aug. 24, 1994

Related U.S. Application Data

[63] Continuation of Ser. No. 952,758, filed as PCT/DK91/00131, May 14, 1991, abandoned.

[30] Foreign Application Priority Data

May 14, 1990 [DK] Denmark .................................. 1194/90

[51] Int. Cl.⁶ .................................................. A61M 37/00
[52] U.S. Cl. .................................. 604/5; 604/4; 604/403; 604/408
[58] Field of Search .......................... 604/4, 5, 6, 403, 604/407, 408, 409, 410; 210/321.62, 321.72, 321.78

[56] References Cited

U.S. PATENT DOCUMENTS

| | | |
|---|---|---|
| 3,064,647 | 11/1962 | Earl . |
| 3,078,847 | 2/1963 | Wandell et al. . |
| 3,223,083 | 12/1965 | Cobey . |
| 3,799,342 | 3/1974 | Greenspan . |
| 3,870,042 | 3/1975 | Viguier . |
| 3,908,893 | 9/1975 | Williams . |
| 3,911,918 | 10/1975 | Turner . |
| 3,932,277 | 1/1976 | McDermott et al. . |
| 3,982,691 | 9/1976 | Schultz . |
| 3,986,506 | 10/1976 | Garber et al. . |
| 4,086,924 | 5/1978 | Latham, Jr. . |
| 4,141,887 | 2/1979 | Seufert . |
| 4,300,717 | 11/1981 | Latham, Jr. . |
| 4,359,049 | 11/1982 | Redl et al. . |
| 4,471,888 | 9/1984 | Herb et al. . |
| 4,530,691 | 7/1985 | Brown . |
| 4,566,610 | 1/1986 | Herb et al. . |
| 4,596,657 | 6/1986 | Wisdom . |
| 4,608,178 | 8/1986 | Johansson et al. . |
| 4,666,429 | 5/1987 | Stone . |
| 4,668,399 | 5/1987 | Duggins . |
| 4,714,457 | 12/1987 | Alterbaum . |
| 4,729,829 | 3/1988 | Duggins . |
| 4,735,616 | 4/1988 | Eibl et al. . |
| 4,735,726 | 4/1988 | Duggins . |
| 4,767,396 | 8/1988 | Powers . |
| 4,769,150 | 9/1988 | Ramstack . |

(List continued on next page.)

FOREIGN PATENT DOCUMENTS

| | | |
|---|---|---|
| 514223 | 12/1978 | Australia . |
| 552883 | 6/1986 | Australia . |
| 446713 | 9/1991 | European Pat. Off. . |
| 505962 | 3/1992 | European Pat. Off. . |
| 3920694 | 1/1991 | Germany . |
| WO88/02259 | 4/1988 | WIPO . |

*Primary Examiner*—Paul B. Prebilic
*Attorney, Agent, or Firm*—Willian Brinks Hofer Gilson & Lione

[57] ABSTRACT

An apparatus for preparing a concentrate of coagulation factors, such as fibrinogen, from a blood sample, comprises a first chamber (14) for collection and separation of said blood sample so as to separate a plasma fraction, and a second chamber (15) for collection of said plasma fraction through a tubing member (22, 30) and a valve (24) and for precipitation of said concentrate. The apparatus comprises furthermore a removable syringe (36) for receiving the concentrate from the second chamber (15) through a tubing member (32). The first and the second chamber (14, 15) are partially defined by the same integrally formed solid container wall (2) and comprise a common partition. The first chamber (14) is further defined by a piston (4) displaceable both in connection with the blood sample collection and the transfer of said plasma fraction to the second chamber (15) and in connection with returning said plasma fraction to the first chamber (14) upon the precipitation of the concentrate.

34 Claims, 6 Drawing Sheets

U.S. PATENT DOCUMENTS

| | | |
|---|---|---|
| 4,784,157 | 11/1988 | Halls et al. . |
| 4,795,441 | 1/1989 | Bhatt . |
| 4,810,378 | 3/1989 | Carmen et al. . |
| 4,818,386 | 4/1989 | Burns . |
| 4,828,716 | 5/1989 | McEwen et al. . |
| 4,856,533 | 8/1989 | Anraku et al. .......................... 604/403 |
| 4,902,281 | 2/1990 | Avoy . |
| 4,902,286 | 2/1990 | Ranoux .................................... 604/403 |
| 4,934,827 | 6/1990 | Taschke et al. . |
| 5,024,613 | 6/1991 | Vasconcellos et al. .................... 604/4 |
| 5,030,215 | 7/1991 | Morse et al. . |
| 5,100,372 | 3/1992 | Headley . |
| 5,137,181 | 8/1992 | Keller . |

APPARATUS FOR PREPARING A CONCENTRATE OF COAGULATION FACTORS FROM A BLOOD SAMPLE

This application is a continuation of application Ser. No. 07/952,758, filed as PCT/DK91/00131, May 14, 1991, now abandoned.

TECHNICAL FIELD

The invention relates to an apparatus for preparing a concentrate of coagulation factors, such as fibrinogen, from a blood sample, said apparatus comprising a first chamber for collection and separation of said blood sample so as to separate a plasma fraction, a second chamber for collection of said plasma fraction through a tubing member and a valve and for precipitation of said concentrate, as well as a removable syringe for receiving said concentrate from the second chamber through a tubing member.

BACKGROUND ART

Inter alia U.S. Pat. No. 4,714,457 discloses a method of preparing coagulation factors, such as fibrinogen, fibronectin, factor VIII and factor XIII from blood by centrifuging a blood sample in such a manner that said sample is separated into a plasma fraction and a cell-containing fraction, said cell-containing fraction inter alia containing platelets (thrombocytes), white blood cells (leukocytes) and red blood cells (erythrocytes). The coagulation factors are subsequently extracted from the plasma fraction by way of for instance cryoprecipitation or by means of a precipitation-promoting agent, such as ethanol. The extract consists mainly of fibrinogen, and by adding a suitable enzyme, such as thrombine, it can be used as tissue glue for instance in connection with operation wounds. When combined with thrombine, the fibrinogen forms fibrin like in nature, said fibrin forming an insoluble network of fibre-like material, which in connection with a wound healing process forms a sort of tissue glue connecting the wound surfaces. Therefore, a concentrate of coagulation factors consisting mainly of fibrinogen has turned out to have an extremely favourable effect on healing of operation wounds.

According to the above U.S. patent specification the concentrate of coagulation factors is prepared by means of various bags, the various fractions being transferred to said bags during the various steps of the process. Such a system of bags is a so-called open system involving a risk of infection and contamination of the personnel.

PCT/DK87/00117 describes an apparatus rendering it possible to prepare a concentrate of coagulation factors from blood from a single person (autologue blood), i.e. the same person who is to use the prepared composition later on in connection with an operation, whereby the risk of dissemination is avoided. The apparatus presents a so-called closed system avoiding the risk of infection and contamination of the personnel. The apparatus comprises a plurality of syringes or containers interconnected by means of valves and loose tubings with the result that it is rather difficult to handle.

DISCLOSURE OF INVENTION

The object of the invention is to provide an apparatus for the preparation of a concentrate of coagulation factors from autologue blood, where the apparatus is simple to handle.

The apparatus according to the invention is characterised in that the first and the second chamber are partially defined by the same integrally formed solid container wall and comprise a common partition, and that the first chamber is further defined by a piston displaceable both in connection with said blood sample collection and transfer of said plasma fraction to the second chamber and in connection with returning said plasma fraction to the first chamber upon the precipitation of the concentrate. The resulting apparatus is relatively easy to handle because it is not necessary to consider loose tubings and interconnected valves.

According to the invention it is particularly preferred that the displaceable piston forms the partition between the first and the second chamber, whereby the apparatus is particularly compact.

Moreover according to the invention the piston rod of the piston may comprise a thread at the end opposite the piston, said thread engaging a thread on an activating means rotatably connected to the solid container wall. As a result, the piston can be easily moved during the transfer of the plasma fraction from the first chamber to the second chamber and back again after the precipitation of the concentrate, and without thereby causing a movement of the apparatus to such a degree that the separations carried out are destroyed. Furthermore, the piston is relatively easily caused to move even though it should have stuck in the resting position during storing. Accordingly, a simple and reliable handling of the apparatus is obtained.

According to the invention it is particularly preferred that the container wall is circular-cylindrical, and that the activating means is a rotatable ring rotatably snap-engaging the circumferential end rim of the circular cylindrical container wall.

In addition according to the invention, the piston rod may be hollow and adapted to receive the removable syringe communicating with the interior of the second chamber through a flexible tubing and the piston. The resulting apparatus is particularly compact and provides a good protection of the syringe until said syringe is finally filled with the concentrate of coagulation factors. The flexible tubing renders it possible to slightly pull out the syringe so as to faciliate the filling therein of concentrate.

The syringe may according to the invention be received in a closed plastic bag fixedly welded at the end about a length of pipe, which at one outer end is adapted to receive the flexible tubing and at the other inner end is adapted to receive the expelling end of the syringe. As a result, a particularly good sterile protection of the syringe inside the apparatus is obtained.

Furthermore the tubing member between the first and the second chamber may according to the invention comprise a channel extending through the piston, where a rotatable valve-forming blocking means extends transverse to said channel and comprises an activating rod placed outside said channel, said activating rod extending axially through the piston rod and comprising a handle member at the outer free end of said piston rod. In this manner a particularly simple activation is ensured of the valve placed between the first and the second chamber and associated with the tubing member. At the same time the activating members associated with the valve are well protected in the interior of the piston rod during the handling of the apparatus.

As the piston rod is only present in one chamber and not in the other chamber, pressure differences may arise between said first and said second chamber. According to the invention the piston rod may extend through a movable bottom member which at the end farthest from the piston defines the first chamber, said bottom member comprising seal means ensuring a sealing connection with both the piston rod and the adjacent portion of the solid container wall. As a result, the pressure differences between the first and the second chamber are equalized in a particularly simple manner during the movement of the piston.

According to the invention, both the tubing member interconnecting the second chamber and the syringe and the tubing member interconnecting the first chamber and the second chamber may be provided with an inlet/outlet to the second chamber, said inlet/outlet being placed immediately adjacent the solid container wall. In this manner it is rendered possible in a particularly simple manner to efficiently remove the plasma remaining in the second chamber after the precipitation as well as the extracted concentrate.

Finally according to the invention, the container wall may be provided with feeding means for feeding an agent promoting the precipitation of the coagulation factors in the second chamber. As a result, the precipitation is initiated in a simple manner. In addition it is rendered possible to equalize the pressure through said feeding means.

BRIEF DESCRIPTION OF DRAWINGS

The invention is described in greater detail below with reference to the accompanying drawing, in which.

BEST MODE FOR CARRYING OUT THE INVENTION

Figure 1:
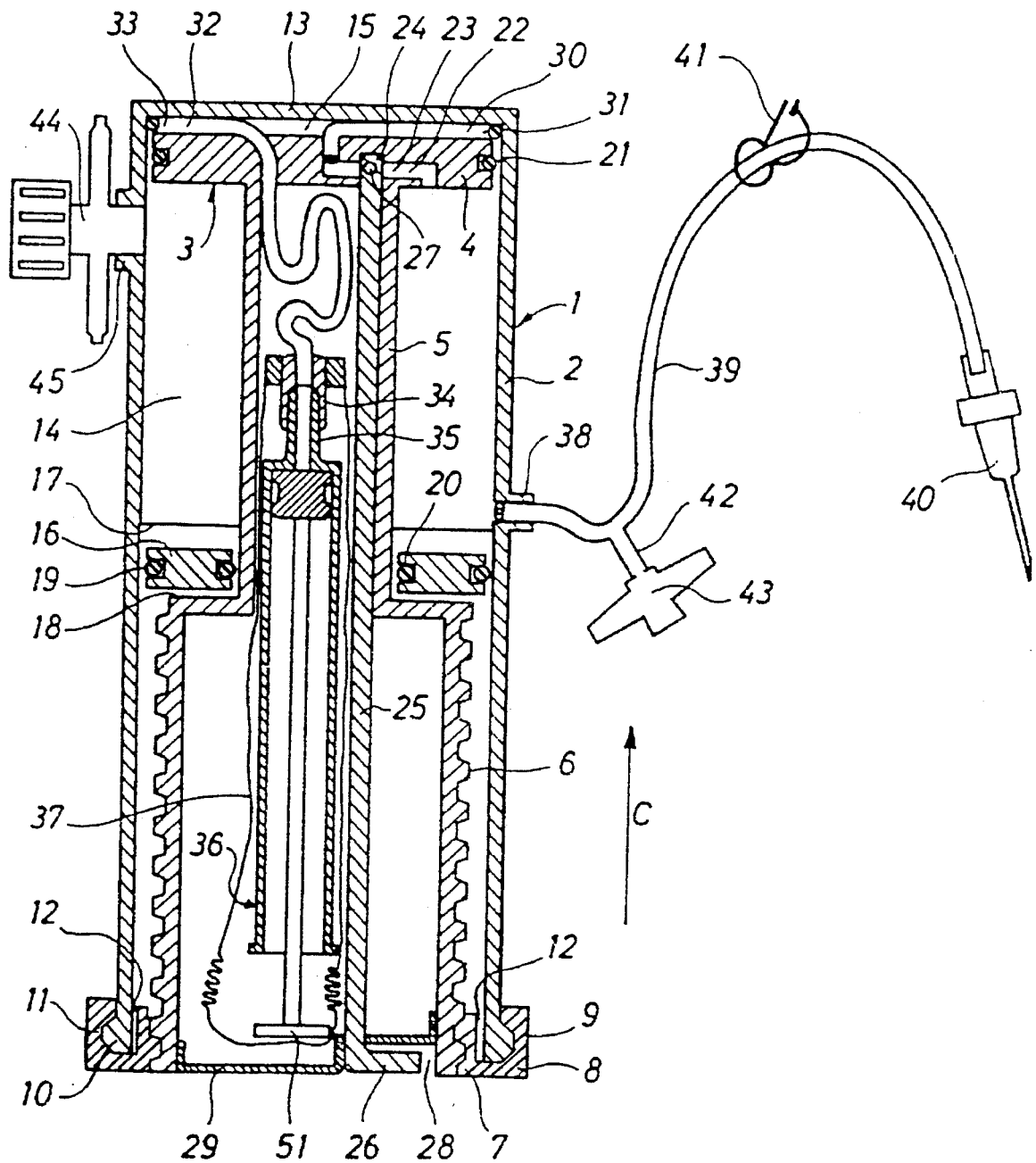
FIG. 1 is an axial side view of a preferred embodiment of an apparatus according to the invention, FIG. 2 corresponds to FIG. 1, but showing the apparatus in use after the precipitation of the concentrate of coagulation factors in a second chamber has taken place, FIG. 3 corresponds also to FIG. 1, but showing the apparatus in use in a succeeding position immediately before the concentrate is filled into a syringe.
Figure 2:
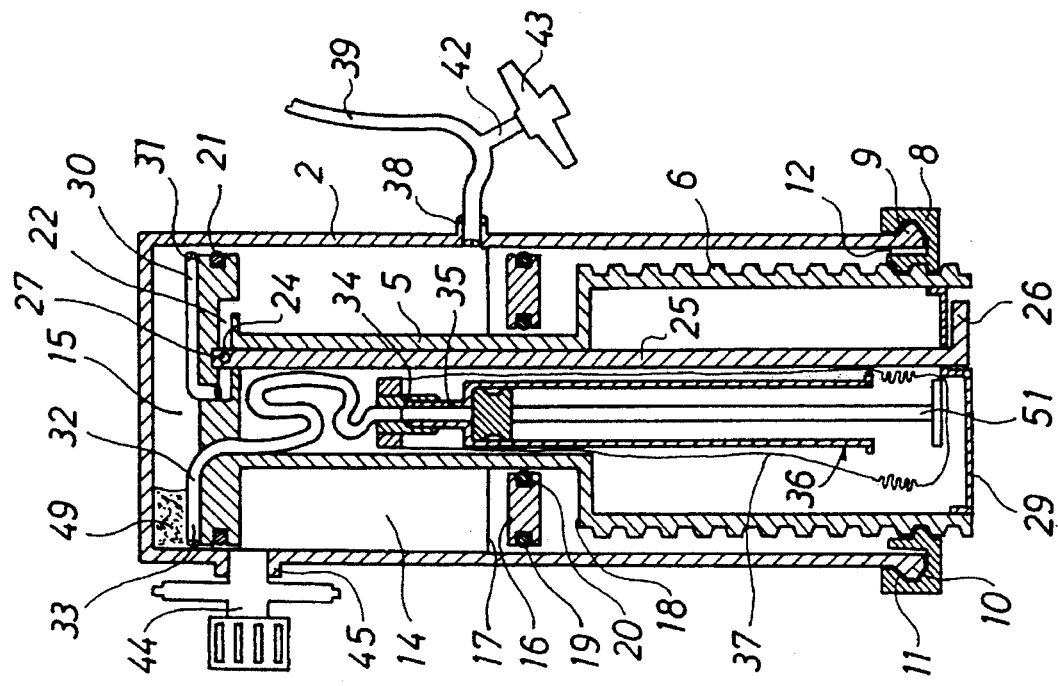
Figure 3:
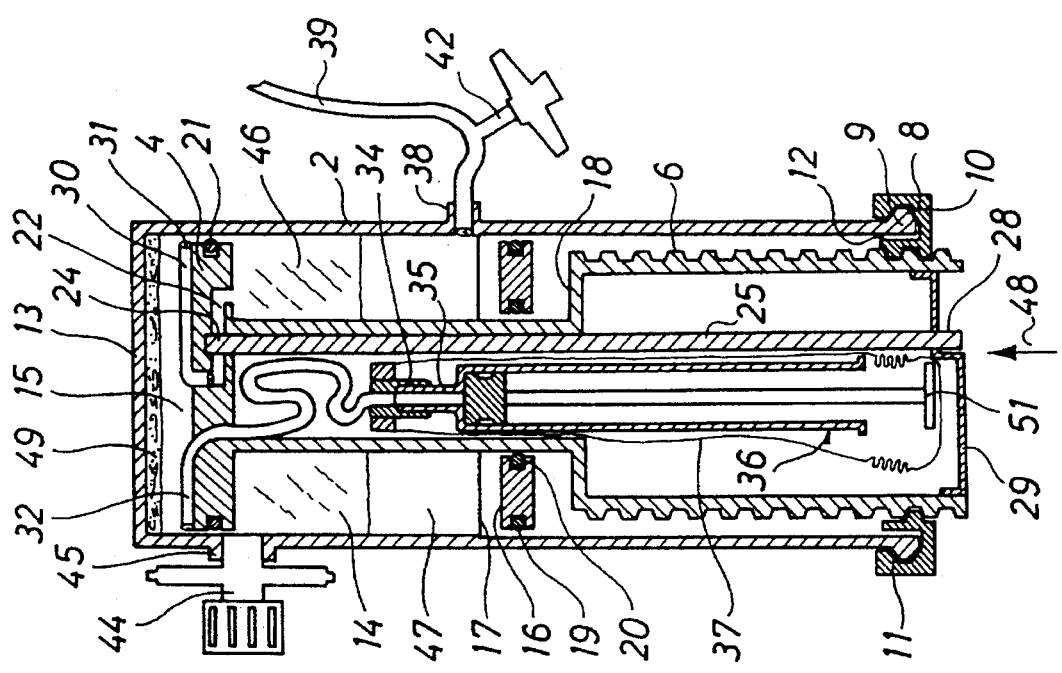

The apparatus shown in FIGS. 1 to 3 comprises a housing designated the general reference numeral 1 and forming a circular-cylindrical container wall 2 about a piston mechanism designated the general reference numeral 3. The piston mechanism 3 comprises a movable piston 4 with a hollow piston rod 5. The piston rod 5 carries at the free end opposite the piston an outer thread 6 engaging an inner thread 7 on a rotatable ring 8. The rotatable ring 8 is caused to rotatably snap-engage the circumferential rim 9 of the container wall 2 at one open axial end thereof. The free rim 9 of the container wall comprises a projecting bead 10 engaging a circumferential groove 11 in a circumferential recess 12 in the rotatable ring, cf. the drawing.

The opposite end of the container wall 2 is closed and forms a bottom wall 13. The piston 4 divides the interior of the housing 1 into a first chamber 14 and a second chamber 15, the volumes of which are regulated by displacement of the piston 4. At the end opposite the piston 4, the first chamber 14 is defined by a movable bottom member 16 loosely arranged within the housing 1 about the piston rod 5. The axial movement of the bottom member is restricted both by a circumferential abutment 17 on the inner side of the container wall and by a radial stop surface 18 shaped on the portion of the piston rod 5 which continues into the portion provided with the thread 6. The bottom member 16 sealingly abuts the inner side of the container wall 2 and the outer side of the piston rod 5, respectively, by means of seal rings 19 and 20. Correspondingly, the piston 4 sealingly abuts the inner side of the container wall 2 by means of a seal ring 21.

The piston 4 is provided with a channel 22 interconnecting the first chamber 14 and the second chamber 15. The channel 22 comprises a radially extending portion 23 housing a blocking means 24. The blocking means is shaped at the end of a rod 25 extending through one side of the piston 4 and all the way through the hollow piston rod 5 to the free end hereof, where it comprises a handle member 26 forming a right angle with said rod 25. The blocking means comprises a transverse bore 27. When the blocking means is turned between two outer positions angularly spaced 90°, the bore can be caused to enter either an open position providing a free passage through the channel 22 or a closed position providing a blocked passage through said channel 22. The blocking means 24 is provided with suitable seal means ensuring a sealing connection with the surrounding surfaces, said seal means not appearing from the drawing for the sake of clarity. As indicated in the drawing, the handle member 26 is placed in a suitable recess 28 in an end cover 29. The end cover 29 is detachably secured in the free end of the hollow piston rod 5 in such a manner that the interior of said rod is closed towards the surroundings. The angular shape of the recess 28 is suitably such that the two different activating positions of the handle member 26 are determined by the walls of said recess.

The channel extending between the first chamber 14 and the second chamber 15 communicates at the end adjacent the second chamber 15 with one end of a tubing 30 secured to the piston. The opposite end of the tubing 30 is placed adjacent the container wall 2.

A second tubing 32 is secured to the side of the piston 4 facing the second chamber 15. The inlet opening 33 of the second tubing 32 in the second chamber 15 is placed adjacent the container wall 2. The second tubing 32 extends through the piston 4 and continues into the interior of the hollow piston rod 5 where a length of said tubing is loosely arranged. The end of the tubing 32 in the interior of the hollow piston 5 is secured to one end of a length of pipe 34, which at the other end sealingly receives the expelling end or lower end 35 of an ordinary 2 ml syringe indicated by the general reference numeral 36.

The syringe 36 is surrounded by a plastic bag 37, which is sealingly secured at the inner end about the above length of pipe 24 by way of welding or glueing. The syringe 36 is detachably secured to the length of pipe 34 by way of friction engagement. The syringe is easily detached from the length of pipe when the bag 37 is broken. The tubing 32 is of such a length that the syringe can be pulled out of the hollow piston rod 5 after removal of the end cover 29. Subsequently, the bag 37 containing the syringe 36 can be removed from the apparatus by cutting off the tubing 32, optionally while said tubing 32 is simultaneously being sealingly glued at the cutting site.

On the side of the abutment 17 of the bottom member 16 closest to the piston 4, a connecting piece 38 is provided for a tubing 39. At the end the tubing 39 carries a needle 40 of a conventional type for puncturing a vein and collecting blood therefrom. The tubing 39 is suitably provided with a tubing clip 41. The tubing 39 is provided with a branching member 42 carrying a filter 43 of a conventional type and allowing addition under sterile conditions of an anticoagulant, such as heparin and/or citrate, to the main tubing 30 and consequently to the first chamber 14 of the apparatus. A similar filter 44 is placed in connection with a connecting piece 45 on the container wall 2 adjacent the bottom wall 13. The second filter 44 renders it possible to add an agent, such as an alcohol in form of for instance ethanol, for promoting the precipitation of a concentrate of coagulation factors in the second chamber 15. In addition, the filter 44 renders it possible to equalize the pressure under sterile conditions. The filters 43 and 44 are only shown diagrammatically, and as mentioned above they are of a conventional type, such as the ones sold by the company Millipore.

A conventional stirrer in form of a magnet may optionally be placed in the second chamber 15, said stirrer being activatable from the outside and used for stirring the contents thereof.

The apparatus according to the invention is operated in the following manner. Initially, a low pressure is established in the first chamber 14 by pressing the piston 4 into the position of FIG. 1. As a result, a single person can easily puncture a vein by means of the needle 40, handle the apparatus without help and ensure that blood is transferred from the patient to the first chamber 14. An anticoagulant is fed to the chamber 14 through the filter 43 before or simultaneously with the above transfer of blood.

When the tubing clip 41 has been closed, the apparatus is placed in a centrifuge in such a manner that the centrifugal force works in the direction opposite the direction indicated by an arrow C in FIG. 1. The centrifuging process has the effect that the blood sample in the first chamber 14 is separated into a plasma fraction and a cell-containing fraction, said plasma fraction being closest to the piston 4. After having activated the handle member 26 of the blocking means 24 so as to open the passage through the channel 22, the piston 4 is pulled out by turning the rotatable ring 8 until the plasma fraction has been transferred to the second chamber 15 through said channel 22 and the tubing 30. Subsequently, the coagulation factors in the plasma fraction are caused to precipitate in a conventionally known manner in the second chamber 15 while being cooled and while ethanol is added through the filter 44. The concentrate of coagulation factors precipitates in the second chamber 15 at a temperature of 0° C. When the apparatus is centrifuged in such a manner that the centrifugal force works in the direction indicated by the arrow C, the precipitated concentrate is caused to settle on the bottom wall 13. Subsequently, the still rather liquid plasma fraction remaining in the second chamber 15 is removed therefrom through the tubing 30 and the channel 22, cf. FIG. 2, by pressing in the piston rod 5 and the piston 4 after opening of the blocking means 24. The plasma fraction remaining in the first chamber has in FIG. 2 been indicated by the reference numeral 46, whereas the cell-containing fraction present in said first chamber is indicated by the reference numeral 47. When the piston 4 is in the position of FIG. 2, a small amount of the liquid plasma fraction still remains in the second chamber 15, the piston rod 5 still being moved in the direction indicated by an arrow 48. It is very important that the entire liquid plasma fraction 45 is removed from the second chamber 15 during the movement of the piston rod, and said removal is facilitated by the apparatus being tilted such that the last amount of liquid ends up in front of the inlet 31 of the tubing 30.

Subsequently, the concentrate 49 remaining in the second chamber 15 is liquidized by the apparatus being heated. Like the previous cooling, the liquidizing is relatively easily and quickly performed because the second chamber 15 abuts the bottom wall 13 and can thereby be subjected to a temperature effect from several sides. As previously mentioned, a stirrer may be present inside the second chamber 15 in form of a magnet which can be activated from the outside and which can facilitate the heating process. When the concentrate 49 has been liquidized, the apparatus is again tilted in such a manner that the concentrate ends up about the inlet 33 to the second tubing 32 communicating with the syringe 36. Then the bottom cover 29 of the piston rod 5 is removed, and the piston rod 51 of the syringe is activated so as to fill the liquid concentrate 49 into the syringe 36. Again the positioning of the inlet 33 of the tubing 32 adjacent the container wall 2 ensures a complete removal of the concentrate 49 from the second chamber 15.

Now the syringe 36 is removed in the manner described above from the remaining portion of the apparatus and is transported with its content of concentrate to the use site, where said concentrate is expelled while the fibrin-forming enzyme, thrombin, is being added.

Before alcohol is added through the filter 44, a small amount (0.3 mm) of plasma from the second chamber 15 can be filled into the syringe. The small amount of plasma is returned to the second chamber 15 after settling of the concentrate and emptying of the remaining alcohol-containing plasma. The amount of plasma returned to the syringe promotes the liquidizing of the concentrate.

Figure 4:
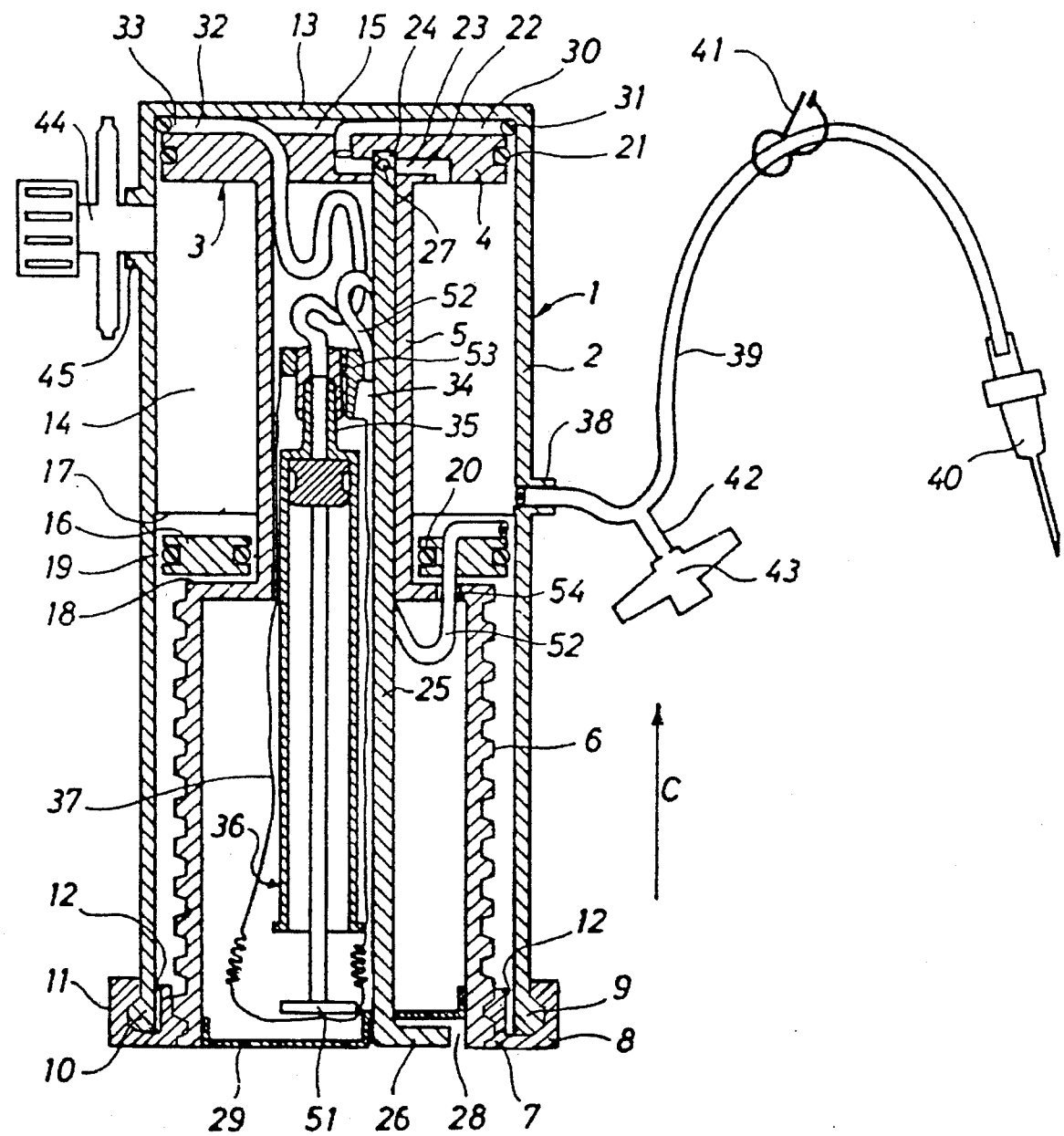
FIG. 4 is an axial side view of a second embodiment of the apparatus according to the invention, FIG. 5 an axial sectional side view of a third embodiment of the invention, where parts have been omitted for the sake of clarity, FIG. 6 on a larger scale a top view of a guide ring used in FIG. 5, FIG. 7 on a larger scale a view of the second embodiment of an end cover used in FIG. 5 and taken along the line VII—VII of FIG. 5, and FIG. 8 an axial, diagrammatic side view of a fourth embodiment of the invention.

The embodiment of the apparatus shown in FIG. 4 corresponds completely to the apparatus of FIGS. 1 to 3 apart from the fact that an additional tubing is inserted between the plastic bag 37 and the first chamber 14. The tubing is indicated by the reference numeral 52, and one end of said tubing is in FIG. 4 connected to a separate length of pipe 53, only a portion of said length appearing from FIG. 4. Like the length of pipe 34, the length of pipe 53 is sealingly surrounded by the plastic bag 37, and inside the bag said length of pipe 53 is adapted to be sealingly connected to the expelling end 35 of the syringe 36. The opposite end of the additional tubing 52 extends loosely through an opening 54 in the wall of the piston rod 5 adjacent the side of the bottom member 16 facing away from the first chamber 14. Subsequently, the additional tubing 52 continues sealingly through the bottom member 16, said tubing 52 being secured to the inner side of said bottom member 16. The free inlet opening of the additional tubing 52 is placed adjacent the cylindrical container wall 2.

The apparatus of FIG. 4 renders it possible to utilize the growth factors present in the cell-containing fraction of the blood. The growth factors referred to are inter alia PDGF (platelet derived growth factors), EGF, FGF, TGF-β IL-1. The growth factors stimulate the healing of wounds because their presence inter alia is responsible for an early start of the re-formation of blood vessels, the collagen synthesis and fibroplasia which is observed in the rim of the wound.

In the apparatus of FIG. 4, the growth factors are concentrated in the first chamber 14 during the centrifuging causing the concentrate 49 to settle in the second chamber 15. The growth factors are concentrated by an agent, such as adrenalin or thrombin, being added before the centrifuging, said agent promoting the separation of said growth factors from the blood cells. The agent is added through the filter 43. As a result, the growth factors are separated in a small amount of plasma remaining in the cell-containing blood fraction despite the previous centrifuging. The centrifuging causes the growth factors to settle on top of the blood cells adjacent the bottom member 16, and accordingly said growth factors are easily filled into the syringe 36 through the tubing 52 by moving said syringe so as to be connected to the length of pipe 53. The orifice of the length of pipe 53 or the tubing 42 may be provided with a closing means not shown in order to prevent an amount of the contents in the first chamber 14 from flowing out through said tubing 52 during the centrifuging.

When the growth factors have been filled into the syringe, said syringe 36 is returned to the length of pipe 34, and the handling of the settled concentrate 49 is continued as described above.

Figure 5:
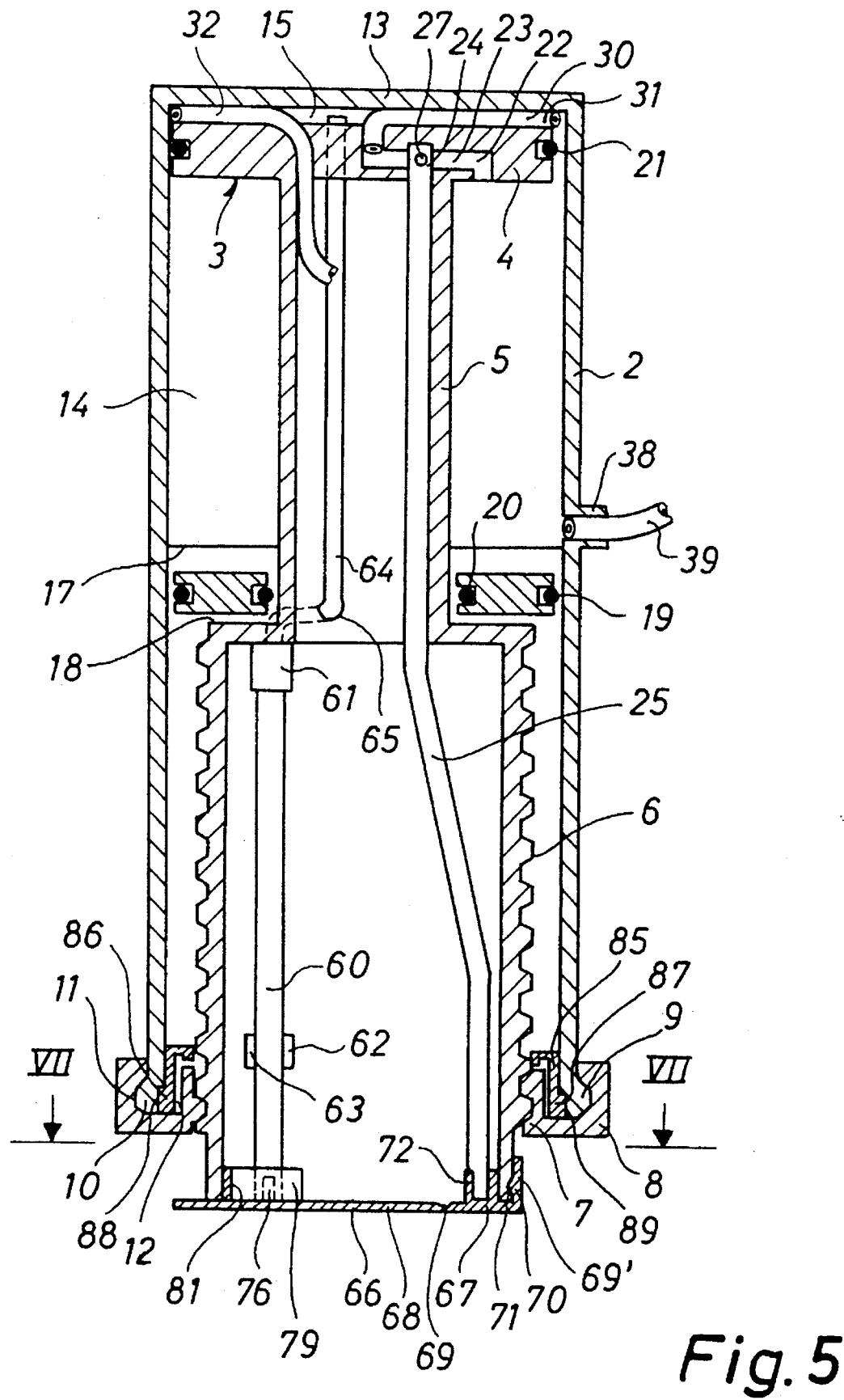

The third embodiment of the invention shown in FIG. 5 is completely identical with the embodiment of FIGS. 1 to 3 apart from a few modifications of the end cover on the piston rod 5 and the sterile filter related to the second chamber 15, said modification being described more detailed below. The identical parts of the embodiment of FIG. 5 and of FIGS. 1 to 3 have been designated the same reference numerals. The plastic bag with the syringe is not included in FIG. 5 for the sake of clarity.

The sterile filter allows feeding of an agent promoting the precipitation of a concentrate of coagulation factors to the second chamber 15, and in FIG. 5 said filter is situated in a tube 60 secured to the inner side of the portion of the piston rod 5 provided with a thread 6. At the innermost end the tube 60 is received in a length of pipe 61 cast integral with the piston rod 5. The tube 60 is further secured between two radially projecting members 62 and 63 also cast integral with said piston rod 5. The tube 60 is connected to a tube 64 inside the length of pipe 61, said tubing 64 extending through the radial wall of the piston rod 5 and through an opening 65 into the narrow portion of said piston rod. Then the tube 64 continues axially along the inner side of the piston rod 5 to the piston 4 where it sealingly extends through a hole and ends on the side of the piston 4 facing the second chamber 15.

The free end of the tube 60 levels substantially with the projecting free end of the piston rod 5. The free end of the piston rod 5 of the present embodiment has been closed by means of an end cover 66 pivotally journalled thereon. The end cover 66 comprises two parts 67 and 68 made of plastics and cast integral with a hinge-forming connecting portion 69, cf. also FIG. 7. The end cover 66 is a substantially plate-shaped body with members projecting perpendicular thereto and cast integral therewith.

The first part 67 of the end cover 66 is provided with a curved skirt 69' of the same radius of curvature as the projecting free end of the piston rod 5. The skirt 69' is adapted to abut the outer side of the piston rod and is provided with a ridge 70 shaped on the inner side thereof and engaging a groove 71 which extends along the outer side of the piston rod 5. Furthermore, a tubular portion 72 is shaped on the first part 67 of the end cover, said tubular portion 72 abutting the inner side of the piston rod 5. The tubular portion 72 is of a rectangular inner cross section. In addition to abutting the inner side of the piston, the tubular portion 72 is furthermore adapted to receive the projecting end of the rod 25 of the blocking means 24, the projecting end of the rod 25 being of the same cross section as the tubular portion 72 on the end cover 66. The blocking means 24 is moved between its two positions by the first part 67 of the end cover 66 being displaced along the rim of the piston rod 5 between two abutments 73 and 74, cf. FIG. 7 indicating the piston rod by dotted lines. As a result, the end cover 66 is easily moved between the two positions about the central axis of the piston rod 5 when the second part 68 thereof has been tipped up.

Figure 7:
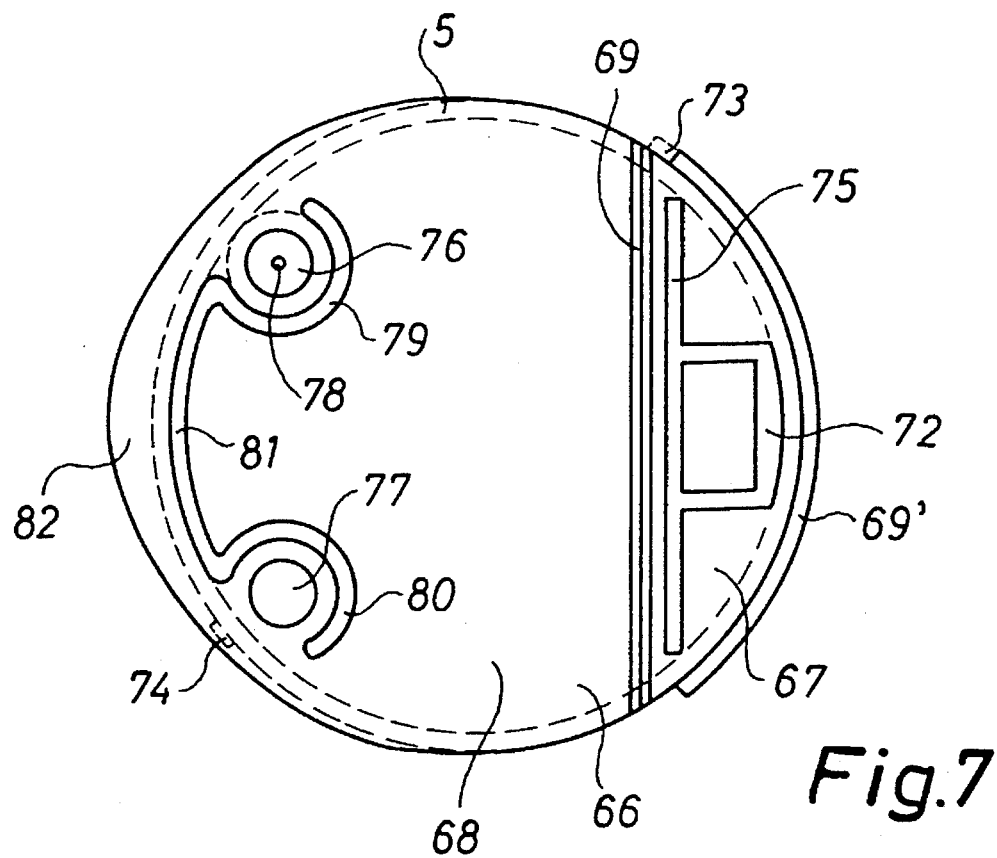

As illustrated in FIG. 7, the inner side of the tubular portion 72 is formed integral with a wall 75 extending parallel to the hinge 69 and ending adjacent the inner side of the piston rod 5. In this manner additional support of the end cover 66 on the piston rod is provided, said end cover being mounted on said piston rod by way of snap-engagement. The wall 75 ensures furthermore that the end cover 66 can move relatively easily between the two abutments 73 and 74 without inference from the plastic bag with the syringe present inside the piston 5.

The second part 66 of the end cover carries two perpendicularly projecting pins 76, 77 situated in such a manner that they can be sealingly received in the free end of the tube 60 in their respective outer position of the end cover. As illustrated in FIG. 7, a through bore 78 extends axially through one pin 76, said bore allowing a bleeding of the second chamber 15 in one of the positions of the end cover 66, viz. when the blocking means 24 is in its closing position.

Furthermore, a wall 79 and 80 is shaped about each pin 76 and 77, said walls being interconnected at a curved wall portion 81 shaped such that it extends along the inner side of the piston rod 5 when the associated part 68 of the end cover 66 is correctly positioned in engagement with the end of the piston rod 5.

The plate-shaped portion of the end cover 66 is substantially circular along a portion of the circumference, cf. FIG. 7, but it is shaped with a portion 82 projecting beyond the circumference, said portion 82 facilitating the handling of the end cover 66.

Figure 6:
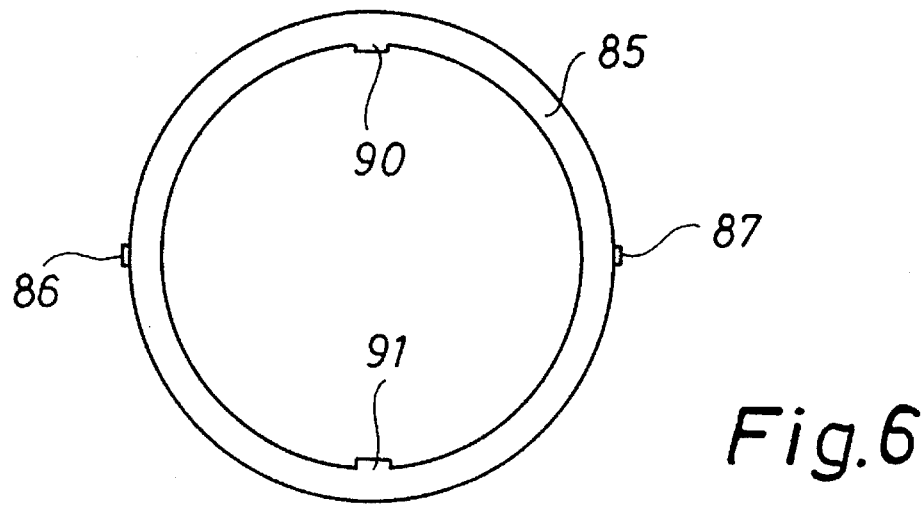

As shown in FIG. 5, a guide ring 85 is mounted within the rotatable ring 8 on the inner side of the cylindrical container wall 2 in this embodiment of the apparatus, said guide ring also appearing from FIG. 6. The guide ring comprises two diametrically opposing pins 86, 87 projecting radially outwards, which are to be received in corresponding recesses 88 and 89 in the container wall, as well as two diametrically opposing pins 90, 91 projecting radially inwards and co-operating with their respective axially extending groove (not shown) in the thread 6 on the piston rod 5. The guide ring 85 ensures that the piston rod 5 and the associated piston are always axially displaced without tending to be turned.

The apparatus of FIG. 5 is used in the same manner as the apparatuses of FIGS. 1 to 4 apart from the fact that the rod 25 of the blocking means 24 is rotated by the end cover 66 being tipped upwards about the hinge 69 and by said end cover being moved between the two abutments 73 and 74 present on the piston rod. The end cover 66 of the apparatus of FIG. 5 is furthermore used for opening or closing the passage through the tube 60 with the sterile filter in the desired positions. As a result, air is always prevented from passing through the tube 60 and the tube 64 to the second chamber 15 when the passage through the channel 22 is open between the two chambers 14 and 15.

Figure 8:
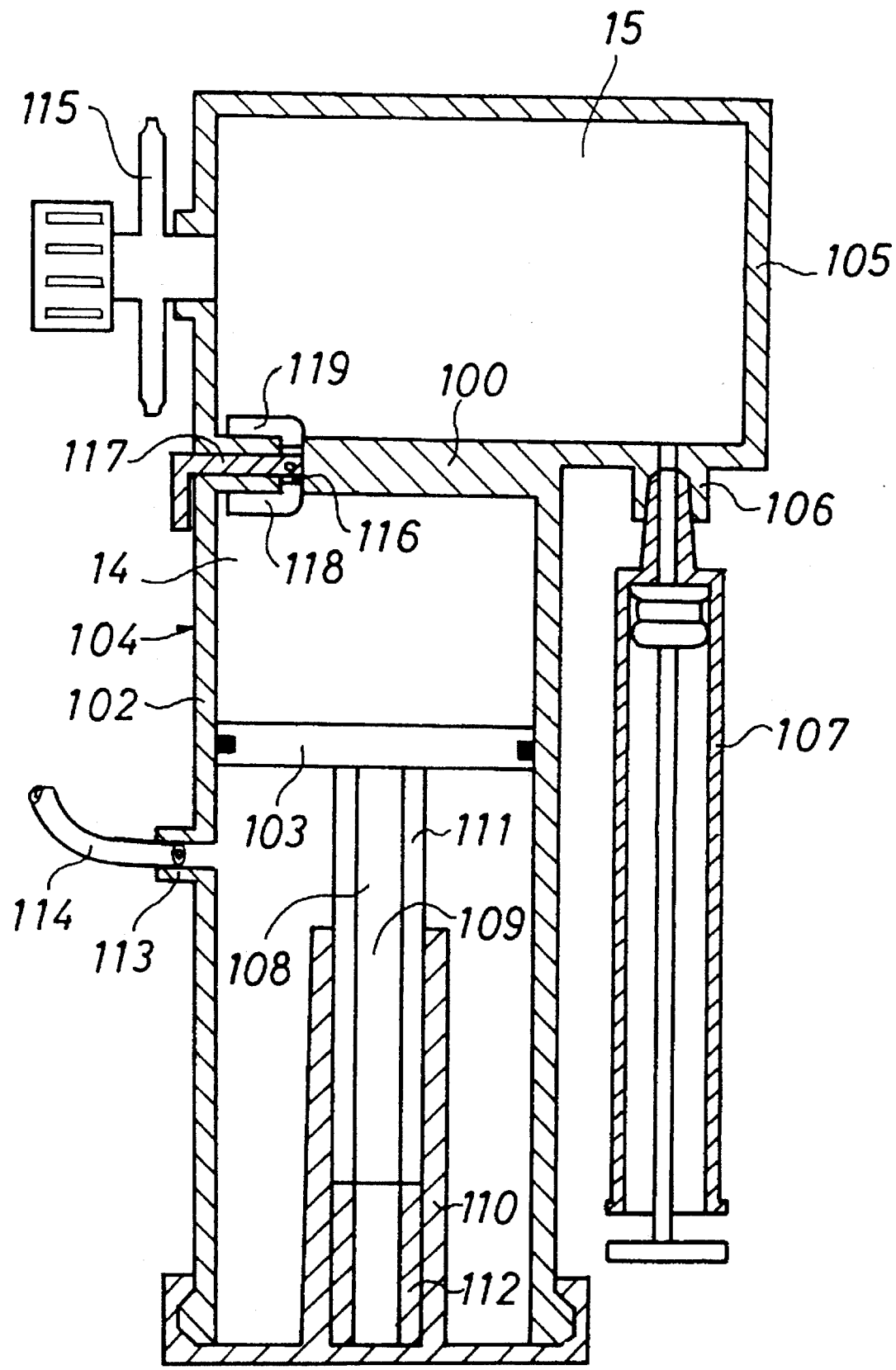

FIG. 8 is a diagrammatic view of a further embodiment of the apparatus according to the invention. As it appears, the two chambers 14 and 15 can also be separated by means of a solid wall 100, the first chamber 14 being provided above a piston 103 in a cylinder 104. The second chamber 15 is shaped on the opposite side of the wall 100, said chamber being defined by solid walls forming a housing 105. The housing 105 is provided with a connecting member 106 allowing mounting of a syringe 107. The piston rod 108 of the piston 103 comprises two parts 109 and 110 interconnected by means of an outer thread 111 and an inner thread 112, respectively. The outermost portion 110 of the piston rod 108 is pivotally connected to the cylinder in such a manner that a rotation of said portion causes an axial displacement of the piston 103. Furthermore, the cylinder 104 comprises a connecting member 113 for the securing of a tubing 114. Like the tubing 39 of FIGS. 1 to 5, the tubing 114 allows feeding of blood to the apparatus through a syringe not described in greater detail. The tubing 114 can also be connected to a filter for the addition of an anticoagulant. Correspondingly, the second chamber 15 is associated with a filter 115 for the addition of an agent promoting the precipitation of a concentrate of coagulation factors.

A channel 116 extends between the two chambers 14 and 15. The channel can be closed by means of a blocking valve 117, and at both ends the channel is connected to a tubing 118 and 119, respectively, ending adjacent their respective wall in the chambers 14 and 15, respectively.

The apparatus of FIG. 8 is used like the previously described apparatuses apart from the fact that the blood is fed through the tubing 114 to the first chamber 14, wherein it is separated into the various fractions by way of centrifuging. By pressing the piston 103 against the solid partition 100, the plasma fraction is transferred to the second chamber 15 when the blocking valve 117 is open. In the second chamber 15, a concentrate of coagulation factors is caused to precipitate in the manner described above. By retracting the piston 103, the liquid residue of the plasma fraction is sucked into the first chamber 14 again whereafter the concentrate of coagulation factors remaining in the second chamber 15 is sucked into the syringe 107.

Possible pressure differences are also in the latter apparatus equalized by means of the sterile filter 115.

The described apparatus can be made of a few and simple components. Substantially all the components can be made of plastics by injection moulding or extrusion, and accordingly it is possible to manufacture a relatively inexpensive apparatus suited to be a disposable apparatus. It is easy to sterilize the above apparatus, and the entire separation of concentrate is carried out under completely sterile conditions in an extremely simple and easy manner.

The invention has been described with reference to a preferred embodiment. Many modifications may, however, be carried out without thereby deviating from the scope of the invention. The channel 22 may for instance optionally be provided with a filter only allowing passage of the plasma fraction. Finally, the plastic tubings 32 and 52 may be integrally shaped with their respective length of pipe 34 and 53, respectively.

We claim:

1. An apparatus for preparing a concentrate of coagulation factors from a blood sample, the apparatus comprising:

a first chamber of variable volume for collection and separation of the blood sample so as to separate a plasma fraction;

a second chamber of variable volume for collection of the plasma fraction and for preparation of the concentrate;

the first and the second chambers being partially defined by the same integrally formed solid container wall;

a displaceable piston which serves as a partition between the first and second chambers, the piston being displaceable in connection with the blood sample collection and the transfer of the plasma fraction between the first and second chambers;

the displacement of the piston causing the volumes of the first and second chambers to vary inversely;

transfer means for transferring the plasma fraction from the first chamber to the second chamber and from the second chamber to the first chamber; and means for opening and closing the transfer means.

2. An apparatus for preparing a concentrate of coagulation factors from a blood sample, the apparatus comprising:

a first chamber for collection and separation of the blood sample so as to separate a plasma fraction, said first chamber having a first end and a second end;

a second chamber for collection of the plasma fraction and for preparation of the concentrate;

a stationary partition between the first and second chambers, said partition defining the first end of the first chamber;

transfer means for transferring the plasma fraction between the first and second chambers;

means for opening and closing the transfer means;

the first and the second chambers being partially defined by the same integrally formed solid container wall;

a displaceable piston defining the second end of the first chamber, the piston being displaceable in connection with the blood sample collection and the transfer of the plasma fraction between the first and second chambers.

3. The apparatus of claim 2 further comprising a syringe for receiving the concentrate from the second chamber.

4. The apparatus of claim 3 wherein the first chamber is also used for the isolation of growth factors from cells and the apparatus further comprises a means for transferring the growth factors from the first chamber to the syringe.

5. The apparatus of claim 2 wherein the transfer means is a tubing member and the means for opening and closing the transfer means comprises a valve.

6. The apparatus of claim 5 wherein the tubing member comprises a channel extending through the partition and a flexible tubing communicating with the channel, the flexible tubing being provided with an inlet which is located immediately adjacent the solid container wall in the second chamber.

7. The apparatus of claim 2 further comprising a filter communicating with the second chamber which allows the addition of agents under sterile conditions that aid in the preparation of the concentrate of coagulation factors.

8. The apparatus of claim 2 further comprising a filter communicating with the first chamber which allows addition of agents under sterile conditions that aid in the release of growth factors from cells.

9. The apparatus of claim 1 which further comprises a removable syringe for receiving said concentrate from the second chamber.

10. The apparatus of claim 1 which further comprises a piston rod for displacement of the piston, the piston rod being attached at one of its ends to the piston.

11. The apparatus of claim 10 wherein the piston rod comprises a thread at the end, not attached to the piston, the thread on the piston rod engaging a thread on an activating means rotatably connected to the solid container wall.

12. The apparatus of claim 23 wherein the container wall is cylindrical and the activating means is a rotatable ring rotatably snap-engaging the circumferential end rim of the cylindrical container wall.

13. The apparatus of claim 10, 11 or 12 wherein the piston rod is hollow and adapted to receive a removable syringe for receiving the concentrate from the second chamber, and the apparatus further comprises such a syringe and a means for transferring the concentrate from the second chamber to the syringe through the piston.

14. The apparatus of claim 13 wherein the means for transferring the concentrate from the second chamber to the syringe comprises a flexible tubing.

15. The apparatus of claim 14 wherein the flexible tubing is provided with an inlet which is located immediately adjacent the solid container wall in the second chamber.

16. The apparatus of claim 14 further comprising a length of pipe which at one outer end is adapted to receive the flexible tubing and at the other inner end is adapted to receive the expelling end of the syringe, the pipe being in receiving relationship with the flexible tubing and the syringe, the syringe being surrounded by a plastic bag sealingly secured about the length of pipe.

17. The apparatus of claim 1 wherein the transfer means is a tubing member and the means for opening and closing the transfer means comprises a valve.

18. The apparatus of claim 10 wherein the transfer means is a tubing member and the means for opening and closing the transfer means comprises a valve.

19. The apparatus of claim 18 wherein the tubing member comprises a channel extending through the piston and the means for opening and closing the transfer means is a rotatable valve-forming blocking means which extends transverse to the channel, the blocking means being carried by an activating rod located outside the channel, the activating rod extending axially through the piston rod.

20. The apparatus of claim 13 wherein the transfer means is a tubing member and the means for opening and closing the transfer means comprises a valve.

21. The apparatus of claim 20 wherein the tubing member comprises a channel extending through the piston and the means for opening and closing the transfer means is a rotatable valve-forming blocking means which extends transverse to the channel, the blocking means being carried by an activating rod located outside the channel, the activating rod extending axially through the piston rod.

22. The apparatus of claim 21 wherein the tubing member further comprises a flexible tubing communicating with the channel, the flexible tubing being provided with an inlet which is located immediately adjacent the solid container wall in the second chamber.

23. The apparatus of claim 21 wherein the end of the piston rod not attached to the piston comprises a circumferentially movable end cover connected to the activating rod, the circumferential movement of the end cover controlling the blocking means.

24. The apparatus of claim 23 wherein the end cover comprises a first part pivotally connected to the free circumferential rim of the piston rod and a second part hingedly connected to the first part, the second part allowing access to the hollow interior of the piston rod when it is tipped outwards.

25. The apparatus of claim 24 wherein the apparatus further comprises a bleeder connection which connects the second chamber with the surroundings, the bleeder connection comprising a tube containing a sterile filter, the tube extending through the piston and the piston rod and ending adjacent the end of the piston rod not attached to the piston, and the second part of the end cover comprises two pins, each pin being adapted to be sealingly received in the free end of the tube when the end cover is moved so that the blocking means is either in an open position permitting the plasma fraction to be transferred between the first and second chambers or when it is in a closed position, and the pin engaging the tube when the blocking means is in the open position comprises a through bleeder bore.

26. The apparatus of claim 10 wherein the first chamber is further defined by a movable bottom member surrounding the piston rod and spaced axially from the piston, the bottom member comprising seal means ensuring a sealing connection with both the piston rod and the adjacent portion of the solid container wall.

27. The apparatus of claim 13 further comprising a movable bottom member surrounding the piston rod and spaced axially from the piston which defines the first chamber, the bottom member comprising seal means ensuring a sealing connection with both the piston rod and the adjacent portion of the solid container wall.

28. The apparatus of claim 9 wherein the first chamber is also used for the isolation of growth factors from cells and the apparatus further comprises a means for transferring the growth factors from the first chamber to the syringe.

29. The apparatus of claim 13 wherein the first chamber is also used for the isolation of growth factors from cells and the apparatus further comprises a means for transferring the growth factors from the first chamber to the syringe.

30. The apparatus of claim 27 wherein the first chamber is also used for the isolation of growth factors from cells and the apparatus further comprises a means for transferring the growth factors from the first chamber to the syringe.

31. The apparatus of claim 30 wherein the means for transferring the growth factors to the syringe comprises a flexible tubing, the flexible tubing having an inlet placed immediately adjacent the container wall in the first chamber, the flexible tubing being secured to the side of the bottom member facing the interior of the first chamber, the flexible tubing sealingly extending through the bottom member, and the flexible tubing having a coupling means allowing the syringe to be coupled thereto.

32. The apparatus of claim 31 wherein the coupling means is a length of pipe.

33. The apparatus of claim 1 further comprising a filter communicating with the second chamber which allows the addition of agents under sterile conditions that aid in the preparation of the concentrate of coagulation factors.

34. The apparatus of claim 1 further comprising a filter communicating with the first chamber which allows addition of agents under sterile conditions that aid in the release of growth factors from cells.

* * * * *

UNITED STATES PATENT AND TRADEMARK OFFICE
CERTIFICATE OF CORRECTION

PATENT NO. : 5,480,378
DATED : January 2, 1996
INVENTOR(S) : Ulla Weis-Fogh et al.

It is certified that error appears in the above-indentified patent and that said Letters Patent is hereby corrected as shown below:

Col. 10,

In claim 12, line 58, delete "23" and substitute --11--.

Signed and Sealed this

Eleventh Day of February, 1997

Attest:

BRUCE LEHMAN

*Attesting Officer*   *Commissioner of Patents and Trademarks*